(12) United States Patent
Arieli et al.

(10) Patent No.: US 9,250,133 B2
(45) Date of Patent: Feb. 2, 2016

(54) SPECTRAL IMAGING CAMERA AND APPLICATIONS

(75) Inventors: Yoel Arieli, Jerusalem (IL); Yosef Weitzman, Tel-Aviv (IL)

(73) Assignee: ADOM, ADVANCED OPTICAL TECHNOLOGIES LTD., Lod (IL)

( * ) Notice: Subject to any disclaimer, the term of this patent is extended or adjusted under 35 U.S.C. 154(b) by 0 days.

(21) Appl. No.: 13/108,040

(22) Filed: May 16, 2011

(65) Prior Publication Data

US 2011/0216324 A1     Sep. 8, 2011

Related U.S. Application Data

(63) Continuation of application No. 11/909,863, filed as application No. PCT/IL2006/000389 on Mar. 29, 2006, now abandoned.

(60) Provisional application No. 60/666,153, filed on Mar. 29, 2005.

(30) Foreign Application Priority Data

Mar. 27, 2006    (IL) .......................................... 174590

(51) Int. Cl.
*G01J 3/45*         (2006.01)
*G01B 9/02*        (2006.01)

(52) U.S. Cl.
CPC .... *G01J 3/45* (2013.01); *G01B 9/02* (2013.01)

(58) Field of Classification Search
CPC ..................................... G01J 3/45; G01B 9/02
USPC .................................................. 356/451–456
See application file for complete search history.

(56) References Cited

U.S. PATENT DOCUMENTS

| | | | | |
|---|---|---|---|---|
| 5,488,474 | A | * | 1/1996 | Fateley et al. ................. 356/326 |
| 5,565,986 | A | * | 10/1996 | Knuttel ......................... 356/456 |
| 6,046,808 | A | * | 4/2000 | Fateley ......................... 356/330 |
| 6,052,188 | A | | 4/2000 | Fluckiger et al. |
| 6,747,742 | B1 | * | 6/2004 | Verma ........................... 356/454 |
| 2002/0027661 | A1 | * | 3/2002 | Arieli et al. ................... 356/512 |
| 2002/0057431 | A1 | * | 5/2002 | Fateley et al. ................ 356/330 |
| 2004/0179202 | A1 | | 9/2004 | Sezginer |
| 2005/0007603 | A1 | * | 1/2005 | Arieli et al. ................... 356/601 |

FOREIGN PATENT DOCUMENTS

| | | |
|---|---|---|
| WO | WO-99/04246 A1 | 1/1999 |
| WO | WO-02/27285 A1 | 4/2002 |
| WO | WO-2004/026198 A2 | 4/2004 |

* cited by examiner

*Primary Examiner* — Tarifur Chowdhury
*Assistant Examiner* — Jonathon Cook
(74) *Attorney, Agent, or Firm* — Sughrue Mion, PLLC

(57) ABSTRACT

There is provided a method for analyzing optical properties of an object, including utilizing a light illumination having a plurality of amplitudes, phases and polarizations of a plurality of wavelengths impinging from the object, obtaining modified illuminations corresponding to the light illumination, applying a modification to the light illumination thereby obtaining a modified light illumination, analyzing the modified light illumination, obtaining a plurality of amplitudes, phases and polarizations maps of the plurality of wavelengths, and employing the plurality of amplitudes, phases and polarizations maps for obtaining output representing the object's optical properties. An apparatus for analyzing optical properties of an object is also provided.

8 Claims, 4 Drawing Sheets

SPECTRAL IMAGING CAMERA AND APPLICATIONS

CROSS-REFERENCED TO RELATED APPLICATIONS

This application is a continuation of U.S. patent application Ser. No. 11/909,863, filed Sep. 27, 2007 (published as US 2008/0158550, now abandoned), which was a national stage application (under 35 U.S.C. 371) of PCT/IL2006/000389 filed Mar. 29, 2006 (published as WO/2006/103663), which claims benefit of U.S. provisional application 60/666,156 filed Mar. 29, 2005, and Israeli application 147590 filed Mar. 27, 2006.

The present invention relates to a spectral imaging camera and applications, and more particularly, to a method and apparatus for analyzing optical properties of an object.

The invention is concerned with a method and an apparatus for enhancing the performance of optical measurement systems by combining them with a spectral imaging camera and providing the ability for analyzing the spectral content of the measured light.

A combination of a spectral imaging camera with some other optical systems such as common-path interferometer, array of micro-confocal microscope and imaging Ellipsometer, can enhance the capability, performance and accuracy of the original optical systems, on one hand, and the performance of the spectral imaging camera, on the other hand. In another aspect of the invention, using new algorithms simplifies the hardware of the spectral imaging camera and provide more data on the measured object.

BACKGROUND OF THE INVENTION

The spectral behavior of light reflected from substrates has been long used for characterizing the substrate's characteristics in scientific, chemical, industrial and forensic applications. A spectral imaging camera and imaging spectrometers must be utilized when the polychromatic light in the 2-D field of view is measured simultaneously. There are numerous optical designs for realizing a spectral imaging camera or imaging spectrometers, such as Sagnac interferometer, Mach-Zender interferometer, Michelson interferometer, Twyman-Green interferometer, Fabry-Perot interferometer, Fourier Transform Spectrometer, dispersive spectrometers, and others. There are many optical methods to measure substrate and multiplayer thicknesses by measuring the spectrum of light reflected from a substrate. These optical methods can, in general, be divided into two categories: Ellipsometry and Spectroscopy. The main difference between Ellipsometry and Spectroscopy is that in Spectroscopy only the amplitude information of the reflected light from the measured object is processed while in Ellipsometry, the measured object is illuminated with oblique illumination and the phase information of the reflected light is processed as well. Both the Ellipsometry and Spectroscopy methods can use polychromatic light that is measured by spectrophotometers. For measuring a complete 2-D field of view of a substrate simultaneously (i.e. with no point- or line-scanning), an imaging Ellipsometry and imaging Spectroscopy should be applied.

It is therefore an object of the present invention to provide an improved optical measurement system by combining spectral imaging cameras or spectral imagers with other optical measurement systems in order to provide the capability for spectral analysis of optical systems.

It is a further object of the present invention to provide new algorithms that simplify the hardware of the spectral imaging camera and provide more data on the measured object.

SUMMARY OF THE INVENTION

In accordance with the present invention there is provided a method for analyzing optical properties of an object, comprising utilizing a light illumination having a plurality of amplitudes, phases and polarizations of a plurality of wavelengths, impinging from said object, obtaining modified illuminations corresponding to said light illumination, applying a modification to said light illumination thereby obtaining a modified light illumination, analyzing said modified light illumination, obtaining a plurality of amplitudes, phases and polarizations maps of said plurality of wavelengths, and employing said plurality of amplitudes, phases and polarizations maps for obtaining output representing the object's optical properties.

The invention further provides an apparatus for analyzing optical properties of an object, comprising means for utilizing a light illumination having a plurality of amplitudes, phases and polarizations of a plurality of wavelengths, impinging from said object, means for obtaining modified illuminations corresponding to said light illumination, means for applying a modification to said light illumination thereby to obtain a modified light illumination, means for analyzing said modified light illumination, means for obtaining a plurality of amplitudes, phases and polarizations maps of said plurality of wavelengths, and means employing said plurality of amplitudes, phases and polarizations maps for obtaining an output indicating said object's optical properties.

Embodiments of the present invention provide methods and apparatuses for combination of spectral imaging cameras or spectral imagers with other optical measurements systems, in order to provide the capability for spectral analysis to the original optical systems. In another aspect, the present invention provides methods for using new algorithms that simplify the hardware of the spectral imaging camera.

In accordance with one embodiment of the present invention, a method is provided for combination of spectral imaging camera, or spectral imager, with chromatic aberrated interferometer. By collecting images of coherence functions of different spectral bands at different depths of the object, the different depths of the object can be measured without the need for scanning.

In accordance with another embodiment of the present invention, the spectral imaging camera or spectral imager is used for decomposition of sub-pixel details in a 2-D field-of-view in an imaging system or imaging interferometry or imaging Ellipsometry.

In accordance with another embodiment of the present invention, the spectral imaging camera or spectral imager is combined with a 2-D array of confocal microscopes in order to measure a 2-D object's surface simultaneously.

In accordance with another embodiment of the present invention, the spectral imaging camera or spectral imager is combined with chromatic aberrated optical system in order to measure a 2-D object's surface simultaneously by determining each spectral band's focus.

In accordance with another embodiment of the present invention, the spectral imaging camera or spectral imager is combined with a chromatic abenated optical system, in order to create an optical system with different focuses each for each spectral band.

In accordance with another embodiment of the present invention, the spectral imaging camera or spectral imager is combined with Imaging Ellipsometry optical system.

In accordance with another embodiment of the present invention, the spectral imaging camera or spectral imager is combined with an Imaging interferometer, in order to provide the interferometric data by means of processing the spectral data.

In accordance with another embodiment of the present invention, the spectral imaging camera or spectral imager is combined with a common-path interferometer, in order to provide a vibrations insensitive interferometer.

In accordance with another embodiment of the present invention, the spectral imaging camera or spectral imager is used for enhancing thermal contrast by measuring temperature gradients.

In accordance with another embodiment of the present invention, the spectral content of light in each pixel in a spectral imaging camera is processed by means of proper conditions for solving matrices in accordance with Fredholm equation of the first kind and Hadamard matrices.

BRIEF DESCRIPTION OF THE DRAWINGS

The invention will now be described in connection with certain preferred embodiments with reference to the following illustrative figures, so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 illustrates an embodiment of a spectral imaging optical system, in accordance with the present invention;

FIG. 2 illustrates an embodiment of an optical apparatus in which an imaging Ellipsometry system is combined with a spectral imaging optical system;

FIG. 3 illustrates an embodiment of an optical apparatus in which a notch filter is introduced in the light path, in accordance the present invention;

FIG. 4 illustrates an optical apparatus in which a 2-D array of chromatic Confocal Microscopes is combined with a spectral imaging optical system, in accordance with the present invention;

FIG. 5 illustrates an optical system with high numerical aperture and with high chromatic aberration, in accordance with the present invention;

FIG. 6 illustrates an optical apparatus in which a chromatic aberrated interferometer is combined with a spectral imaging optical system, in accordance with the present invention, and FIG. 7 illustrates a spectral imaging camera system, in accordance with a further embodiment of the present invention.

DETAILED DESCRIPTION OF PREFERRED EMBODIMENTS

Figure 1:
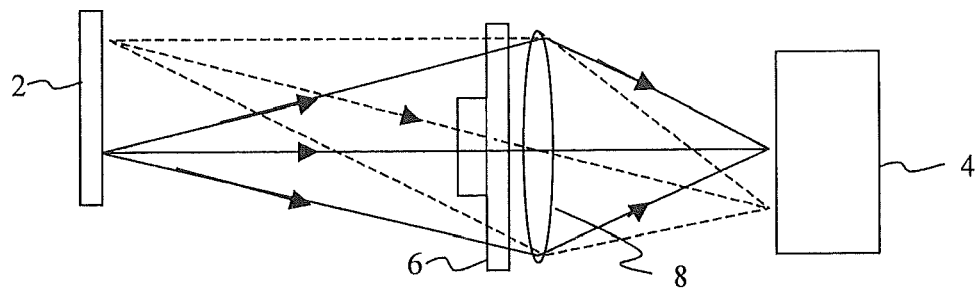

With reference to FIG. 1, an embodiment of a spectral imaging optical system is described. The light from each point in an object 2 is imaged to the image plane to form the image. A camera 4 is placed in the image plane. On its path, the wavefront originated from each point of the object propagates through a spatial light modulator (SLM) 6, delaying part of the wavefront (related to the specific point of the object) relative to the other part. The SLM 6 can be placed at the exit pupil 8 of the optical system or at any other plane in the optical system. If the relative phase retardation for a certain wavelength is half wavelength, a destructive interference arises at the image point for that certain wavelength. The relative phase retardations for other wavelengths, however, are not exactly half wavelength and the interference for other wavelengths is not destructive. The relative phase delay between a part of the wavefront relative to the other part for each wavelength is actually given by:

$$\delta\Phi = \frac{2\pi}{\lambda}\Delta$$

where $\lambda$ is the wavelength and $\Delta$ is the Optical Path Difference between the field regions of the phase shifting device.

When the phase shifting device scans and changes its optical path difference between its field regions progressively, each wavelength in its turn oscillates between destructive and constructive interference states correspondingly. The same holds true for each point in the object separately. The camera grabs many intensity images for many different phase delays. These intensity images can be processed by known algorithms (such as Fourier transform) to obtain the complete spectrum of each imaged point of the object.

This optical scheme maintains a "single optical path", unlike other interferometry schemes where the light is separated to two different paths inside and outside the optical system.

This optical scheme is fundamental and can be implemented for any type of electromagnetic radiation.

Figure 2:
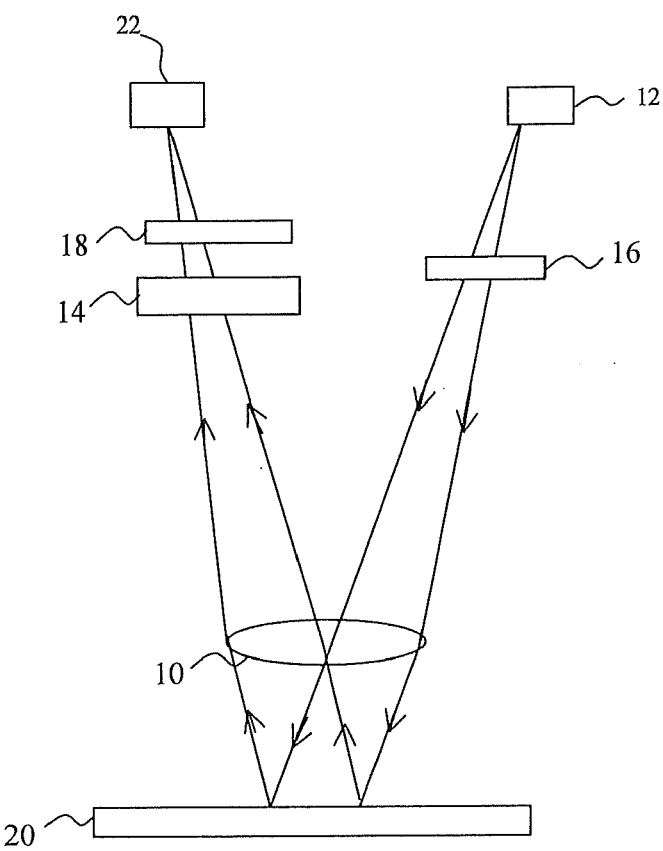

FIG. 2 illustrates an optical apparatus in which an imaging Ellipsometry system is combined with a spectral imaging optical system. The basic Imaging Ellipsometry system consists of an imaging optical system 10, a light source 12, a retardation birefringent plate 14 and polarizers 16 and 18. The light coming from the light source 12 is projected by the optical system 10 obliquely on the object 20. The projected light beam is collimated and propagates obliquely relative to the optical axis of the optical system. The obliquely reflected collimated beam is collected by the optical system and projected onto a CCD camera 22 or any other 2-D array of detectors. On its path, the light beam propagates through a retardation birefringent plate 14 that retards one polarization relative to the other polarization. The retardation birefringent plate 14 and the polarizers 16 and 18 may be rotated in order to attain different phase retardations between the two polarizations. The rotations are performed on the first polarizer 16, the second polarizer 18 or the retardation birefringent plate 14, together or each alone, in accordance with the different methods of Ellipsometry. These different phase retardations between the two polarizations cause different intensities at each point of the object that is imaged on the camera. The different intensities are determined by the relative state of the polarizers and the retardation plate, the phase retardation obtained by the retardation birefringent plate 14 and the phase retardation between the two polarizations obtained by the material at that point. By known algorithms the thicknesses or the refractive indices of the substance at each pixel, can be calculated.

The main drawback of a regular imaging Ellipsometry is that the necessity of oblique illumination limits the field-of-view and the lateral resolution and especially in high magnifications due to limited range of depth of focus. In accordance with the present invention, a method for imaging Ellipsometry is presented, in which the lateral resolution is not diminished due to the limited range of depth of focus, since the whole field-of-view is located in the focal plane of the optical system.

Figure 3:
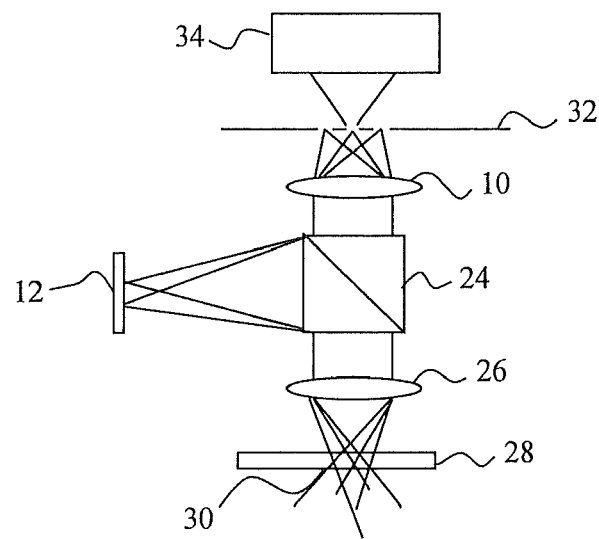

Referring to FIG. 3, an optical apparatus in which a 2-D array of chromatic Confocal Microscopes is combined with a spectral imaging optical system, is described.

The classical monochromatic confocal microscope basically can be considered as being a "single point" viewing system where a point source is imaged on the object. This point on the object is imaged onto a tiny spatial filter. The light passes through the spatial filter only if the point on the object is focused on the spatial filter. The distance from the spatial filter to the object can be measured by the intensity of light. By electromechanically scanning the object surface in the (x, y) direction, the micro-topographic structure of any type of surface is obtained. When working with a polychromatic (on axis) point source and creating intended chromatic aberration, a continuum of (on axis) monochromatic diffraction limited images corresponding to the extent of the effective spectral composition of the light source can then be obtained. As a consequence of the spatio-chromatic filtering performed by the chromatic confocal setup, only an almost monochromatic light beam comes to focus onto the filtering pinhole, which also acts as the entrance port of a spectrometer. The central wavelength of this monochromatic light beam corresponds to the exact distance to the measured object point. By electromechanically scanning the object surface in the (x, y) direction, the micro-topographic structure of any type of surface is obtained.

In the present invention, the electromechanical scanning of the object surface is eliminated by using a spectral imaging camera to process the spectral illumination at each pixel of the field-of-view simultaneously. In the embodiment described in FIG. 3, an array of points of white light sources 12 is imaged through a beam splitter 24 by a lens 26, which has high chromatic aberration on an object 28. Thus, the lens 26 has several focuses 30 each for each wavelength (the figure showing the different focuses for one point light source, only). The light reflected from the object is imaged through the beam splitter 24 via an optical system 10 on an array of small holes 32 and passes to a spectral imaging camera 38. The spectrum of light at each pixel can be processed to immediately obtain the object's surface. The optical apparatus described here can be used to obtain 3-D scenes in a micro- or macro-scale. It should be noted that the optical system described above can also be realized by means of an array of lenses instead of one lens 26, and an array of detectors, without the need for array of pinholes. If the fill-factor of each detector in the array is small, it actually acts as a pinhole, since only the focused radiation of a certain wavelength is focused on the detector and all other wavelengths that are not focused, are spread in the area surrounding the detector.

Figure 4:
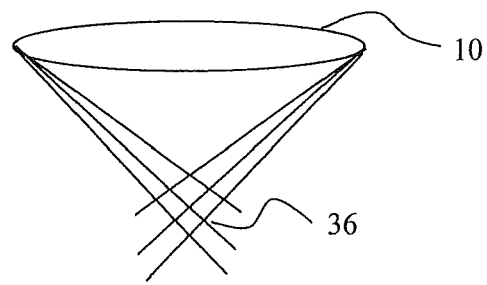

With reference to FIG. 4, an embodiment of an optical system with high numerical aperture, on the one hand, and extended depth of field, on the other hand, is described. In this embodiment, the spectral imaging camera or the spectral imager is combined with an optical system with high numerical aperture and high chromatic aberration. FIG. 4 illustrates an optical system 10 with high numerical aperture and high chromatic aberration. The optical system 10, e.g., a lens, has high numerical aperture and high chromatic aberration which causes many different focuses 36 each for each wavelength. According to this embodiment, the light incoming from an object is processed by a spectral imaging camera, and different images with different wavelengths are obtained. Each image has its own focal length, which is determined by the chromatic aberration of the optical system, and as a result, an extended depth-of-field is attained. This optical system can be an objective lens of a microscope or any other optical system. The chromatic aberration of the optical system can be performed in any optical element in the optical system—before, inside or after the objective lens or any other lens in the optical system. A suitable image-processing algorithm is used for extracting the complete image in a focus condition.

This optical system can be used for many applications that require high numerical aperture and extended depth-of-field at the same time, such as a semiconductor bump inspection in which high optical resolution is required, on the one hand, and on the other hand, the whole bump can be inspected at the same time. Another application that can use optical system with high numerical aperture and extended depth-of-field is semiconductor overlay inspection. In overlay inspection, the registration between several layers, one upon the other, is monitored. The critical dimensions in overlay inspection are close to the limit of the optical resolution, and thus, the depth-of-field is limited. The different layers cannot be seen in focus simultaneously. By using the optical system with high numerical aperture and extended depth as described above, the different layers in overlay inspection can be seen in focus simultaneously and registered in real time. In addition, the spectral analysis of the reflected light simultaneously provides information about the height of each point of the field-of-view that can be utilized as described above.

In another embodiment of the present invention, the addition of a spectral imaging camera to a microscope or any other optical system, can improve the spatial resolution of the optical system. In this scheme, a dispersive optical element is added to the optical system. The dispersive optical element disperses the light impinging from the object, laterally. By means of a spectral imaging camera, many different images in different wavelengths are obtained. These different images are dispersed laterally relative to each other. This lateral dispersion enables the use of super-resolution algorithms as known in the art. By registering the dispersed images by means of a processor unit, each point of the field-of-view is analyzed and compared in all different wavelengths using known super-resolution algorithms.

Figure 5:
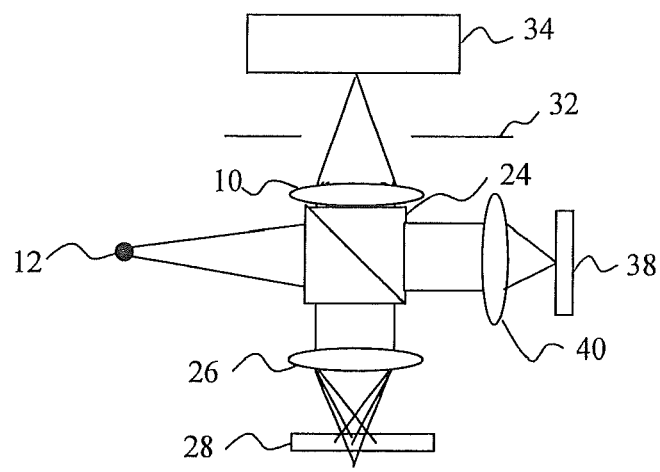

Referring now to FIG. 5, a combination of chromatic aberrated interferometer with a spectral imaging camera or a spectral imager, is described. In the optical apparatus illustrated in FIG. 5, a Linnik interferometer is combined with a spectral imaging camera. In this apparatus, the light incoming from the wideband light source 12 is split by a beam-splitter 24. Part of the light illuminates the object 28 through an objective lens 26, and part of the light impinges on a reference mirror 38 through a lens 40. The objective lens 26 has high chromatic aberration. The light reflected from the object interferes with the light reflected from the reference mirror on an inspected plane where a spectral imaging camera 34 is located. Since the objective lens 26 has high chromatic aberration, each wavelength has its own focal length. By processing the interference pattern on the inspected plane by a spectral imaging camera, different images with different wavelengths are obtained. Each image has its interference pattern due to its wavelength and its own focal length that is determined by the chromatic aberration of the optical system. By analyzing the different interference patterns of the different wavelengths, the height of the object can be calculated.

According to the present invention, no scanning is needed to obtain the heights of the extended object. This idea can be extended and implemented as well in Michelson interferometer, Mirau interferometer and any other interferometer apparatus known in the art.

Figure 6:
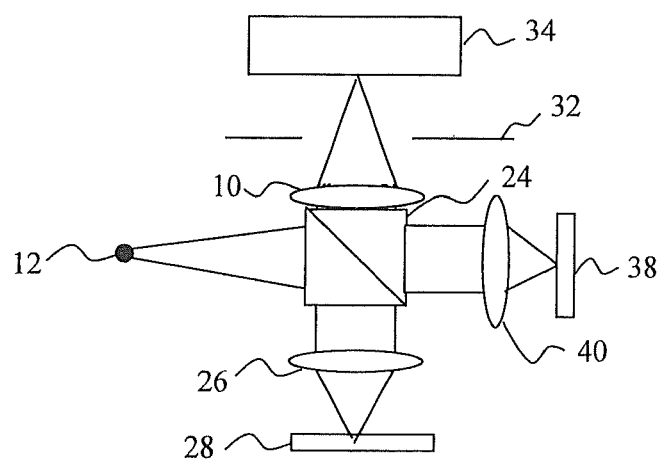

In FIG. 6, a white light interferometer with a spectral imaging camera or a spectral imager, is described. In the embodiment illustrated in FIG. 6, a spectral imaging camera is incorporated with a Linnik White light interferometer to obtain heights, i.e., absolute and relative distance (topography). In a white light interferometer, the light incoming from a white light source 12 is split into two beams by a beam splitter 24. One beam is directed through an objective lens 26 to illuminate the object 28 and the other beam is directed to a reference mirror 38 through a lens 40. The light reflected from the object interferes with the light reflected from the mirror on a certain plane where a spectral imaging camera 34 is located. Due to the short coherence length of the white light, fringes are obtained only when the optical path difference between two beams is very small. The cause for this effect is that the different fringe patterns of the different wavelengths overlap each other and the overall result is that the fringes are blurred. When the optical path difference between two beams is very small, the different fringe patterns of the different wavelengths are still in phase and the fringes are still visible. When the mirror is placed such that the fringes are obtained in the focal plane of the objective lens, the focal plane can be found accurately by analyzing the fringe pattern. Moving the objective or the reference mirror causes the fringe pattern to scan the height of the object, and its contours are obtained.

In an embodiment of the present invention, it is suggested to analyze the intensity that is obtained by white light interferometry at each point of the object by means of a spectral imaging camera. Instead of scanning the height of the measured object with the white light interferometer to obtain contours of heights of the object, as describe above, the spectral analysis of the intensity obtained by white light interferometry can provide the information about the height of the object, without scanning. By spectrally analyzing the intensity obtained by white light interferometry with a spectral imaging camera, the fringe patterns of many different wavelengths can be visualized. By analyzing these different fringe patterns the information about the height of the object can be calculated. This process eliminates the need for moving the objective or the reference mirror to cause the fringe pattern to scan the height of the object.

In another aspect of the invention, new algorithms that simplify the hardware of the spectral imaging camera and provide more data on the measured object, are provided.

Figure 7:
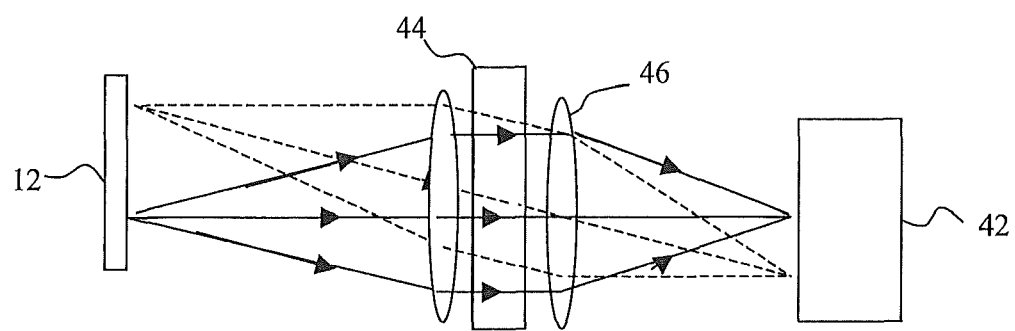

In FIG. 7, a spectral imaging camera in which the spectral content of the light in each pixel of the object viewed by the camera, is retrieved by means of tunable filter, is illustrated.

The overall intensity of light is the sum of the specific intensities of the spectral bands contained in this light, and thus the intensity of light can be described by linear equations. This linear property can be described mathematically by matrices of different kinds, such as Hadamard matrices, or some other kind of matrices, and by Fredholm equation of the first kind. By changing any physical property of any of the different spectral bands and detecting the change of the overall intensity, a set of linear equations can be set and the intensity of each spectral band can be calculated. If the relation between the change of the physical property of the spectral band and the change of its intensity is known, a set of linear equations can be set. By solving this set of linear equations, the intensity of each spectral band can be calculated.

Similarly, the intensity of each spectral band can be obtained by changing any physical property of the optical system observing the light to be measured spectrally on the detector and detecting the change of the overall intensity caused by this change. If the relation between the change of the physical property of the optical system observing the light to be measured spectrally and the change of its intensity on the detector is known, a set of linear equations can be set. By solving this set of linear equations, the intensity of each spectral band can be calculated.

In the embodiment shown in FIG. 7, the change of the physical property, i.e., the transitivity of the optical system, is performed by means of a tunable filter. The light from each point of the object 12 is imaged to the image plane to form the image. A camera 42 is placed in the image plane. On its path, the light originated from each point of the object propagates through a tunable filter 44, which changes its transitivity for the different wavelengths as a function of time. The tunable filter 44 can be placed at the exit pupil 46 of the optical system or at any other plane in the optical system. By measuring the intensity for different states of the notch filter, a set of linear equations can be set. By solving this set of linear equations, the intensity of each spectral band can be calculated. This can be done simultaneously for each detector in an array of detectors where each detector corresponds to each point of the field of view. In one implementation, the tunable filter can be a variable Fabry-Perot interferometer in reflection (not in transmitting mode were only one spectral band is transmitted) where the light that is reflected is detected, the spectral content of the light for each point of the field-of-view can be calculated. In the reflection mode the Fabry-Perot interferometer actually acts as a variable narrow-band filter, transmitting only narrow spectral bands and reflecting all other bands. In another implementation, an Acousto-Optical Tunable Filter (AOTF) is added in the path of light. An AOTF consists of a crystal in which radio frequencies (RF) acoustic waves are used to separate a single wavelength of light from a broadband source. The wavelength of light selected is a function of the frequency of the RF applied to the crystal. Thus, by varying the frequency, the wavelength of the filtered light can be varied. As the acoustic transducer scans the frequencies, a certain wavelength of light is actually attenuated at each acoustic frequency. The AOTF actually acts as a variable narrow-band filter, deflecting narrow spectral bands, and all other bands are transmitted. The transmitted light is detected by an array of detectors each one for each point of the field-of-view.

In another implementation, a stack of a polarizer, a liquid-crystal device and an analyzer are added in the light path. An LC device changes the relative phase retardation difference of two polarizations of light as a function of voltage. Thus, by varying the voltage, the wavelength attenuated by the stack can be varied. As the LC device controller scans the voltage, certain wavelengths of light are attenuated more at each specific voltage and other are attenuated less. The stack actually acts as a variable filter, attenuating some spectral bands, and other bands are transmitted. The transmitted light is detected by an array of detectors each one for each point of the field-of-view.

In another implementation, the change of the a physical property of the optical system is obtained changing the dispersion of one or more of the optical elements, thus varying the spectral characteristics of the optical system. The transmitted light is detected by an array of detectors each one for each point of the field of view. By measuring the intensity for different dispersion variations, a set of linear equations for each point of the field-of-view can be set. Solving this set of linear equations, the intensity of each spectral band for each point of the field of view can be calculated. Such dispersion variations can be created by varying the system aberrations, displacing one or more optical components of the system, etc.

In another implementation, the methods that were described above for calculating the spectral intensities can be implemented also for 1-D case in which the light of the source is coupled into a fiber optics, or the light impinges from the object is coupled into a fiber optics. The physical property of the optical fibers or some other optical component in the optical fiber system can be changed and the overall intensity of light propagating through the fiber can be measured. This variation can be created, for example, by varying the refractive index of a Bragg grating or varying its steps by heating or stretching.

In another embodiment of the present invention, the physical property change that was mentioned above can be obtained by changing the spectral response of the detectors array or in the camera. This spectral response change can be obtained by changing the temperature of the detectors or by changing any other physical or chemical property. This spectral response change can be done simultaneously for each detector in the array of detectors where each detector corresponds to each point of the field-of-view.

In another embodiment of the present invention, the physical property change that was mentioned above can be obtained by changing the spectral characteristics of the light source by changing its temperature or any other physical or chemical property.

According to this approach, higher optical throughput can be obtained by using most of the optical signal while changing only some specific bands each time.

In another aspect of the invention, new algorithms providing more data on the measured object, are provided.

When some physical properties of an object determine its optical complex reflectivity, these physical properties can be measured by analyzing the light reflected by the object. This analysis can be obtained by means of a Spectrometer, Reflectometer, Ellipsometer, Intereferometer or some other optical device. In Spectrometery and Reflectometery just the amplitude of the different wavelengths are measured. In Ellipsometery, the polarization of the reflected light for one or more wavelengths is measured and in Intereferometery the amplitude and phase of the reflected light for one or more wavelengths is measured. By decomposing the signal into its principal frequencies, the lateral variations of the physical property of the object can be determined. When the a Spectral Imaging Camera is combined with a Spectrometer, a Reflectometer, an Ellipsometer, an Intereferometer or some other optical device as described above the Spectral Imaging Camera analyzes spectrally each pixel of the image that corresponds to an array of points in the object.

In accordance with the present invention, decomposing the signal of each detector or pixel in the detectors array into its principal frequencies, enables to determine the lateral variations of the measured physical property of the object within each detector or pixel.

In another aspect of the invention, the present invention can be used for optically, non-contact and remotely identifying hidden objects. When an object is disturbed from its thermal equilibrium by changing the surrounding temperature (raising or lowering), in order to reach again thermal equilibrium, the object emits or absorbs infrared radiation. However, the rate of emitting or absorbing the infrared radiation is different for different bodies and materials according to the different thermal mass, emissivity or other physical characterization. Moreover, this rate of emitting or absorbing of the infrared radiation is a function of both the wavelength that is emitted or absorbed and the temperature. Consequently, by viewing the object in the IR regime in different times, different parts of the object appear with different radiance as a result of the contrast that evolves according to the rate of emitting or absorbing of the infrared radiation. Since this rate of emitting or absorbing of the infrared radiation is function of the wavelength that is emitted or absorbed and the temperature, the contrast is also a function of the wavelength and temperature, and can be different for different wavelengths at different times. It can also be in a different enhancement in different wavelengths at different time.

In accordance with the present invention, using Optical Spectral Imaging to observe the object and to differentiate its spectral radiation or absorbance in different times, can improve the ability to expose hidden objects under cloths or behind a shield, thermally conductive.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. Apparatus for use with a light source configured to direct non-spatially-coherent light toward an object, the apparatus comprising:

an imaging system that comprises:

an optical system for collecting a plurality of wavefronts, the plurality of wavefronts emanating from respective points of the object, as a result of the non-spatially-coherent light being directed toward the object, each of the plurality of wavefronts being composed of multiple spectral bands, each of the spectral bands having a respective amplitude, phase and polarization;

a spectral imaging camera that comprises a plurality of detectors corresponding to the respective points of the object and configured to receive, from the optical system, the wavefronts emanating from the respective points;

a modulator disposed along an optical path that passes between the object and the spectral imaging camera, the modulator being configured to individually modulate each of the wavefronts emanating from the respective points, by, individually, for each of the wavefronts:

causing one or more spectral bands within a first portion of the wavefront that travels along the optical path to interfere with one or more spectral bands within a second portion of the wavefront that travels along the optical path, by applying an optical path difference to the first portion of the wavefront relative to the second portion of the wavefront that is equal for all of the spectral bands of the first portion of the wavefront; and a processing unit configured:

to receive, from each of the detectors, an integrated signal that is representative of the spectral bands within the first and second portions of the wavefront received at the detector, and for each of the wavefronts, to determine an optical property of the point of the object from which the wavefront emanated by analyzing the integrated signal.

2. The apparatus according to claim 1, wherein the modulator is configured to progressively change the optical path difference that is applied to the first portion of the wavefront relative to the second portion of the wavefront.

3. The apparatus according to claim 1, wherein the processing unit is configured to determine the optical property of the point of the object from which the wavefront emanated by calculating an intensity of each spectral band in the wavefront that emanated from the point, by solving a set of matrices that represents the wavefront.

4. The apparatus according to claim 1, wherein the processing unit is configured to determine the optical property of the point of the object from which the wavefront emanated by calculating an intensity of each spectral band in the wavefront that emanated from the point, by solving a Fredholm equation that represents the wavefront.

5. A method for use with a light source configured to direct non-spatially-coherent light toward an object, the method comprising:
   using an optical system, collecting a plurality of wavefronts emanating from respective points of the object, as a result of the non-spatially-coherent light being directed toward the object, each of the plurality of wavefronts being composed of multiple spectral bands, each of the spectral bands having a respective amplitude, phase and polarization;
   using a plurality of detectors corresponding to the respective points of the object, receiving, from the optical system, the wavefronts emanating from the respective points;
   using a modulator disposed along an optical path that passes between the object and the spectral imaging camera, individually modulating each of the wavefronts emanating from the respective points, by, individually, for each of the wavefronts:
   causing one or more spectral bands within a first portion of the wavefront that travels along the optical path to interfere with one or more spectral bands within a second portion of the wavefront that travels along the optical path,
   by applying an optical path difference to the first portion of the wavefront relative to the second portion of the wavefront that is equal for all of the spectral bands of the first portion of the wavefront; and
   using a processing unit:
   receiving, from each of the detectors, an integrated signal that is representative of the spectral bands within the first and second portions of the wavefront received at the detector; and
   for each of the wavefronts, determining an optical property of the point of the object from which the wavefront emanated by analyzing the integrated signal.

6. The method according to claim 5, wherein applying the optical path difference to the first portion of the wavefront relative to the second portion of the wavefront comprises progressively changing the optical path difference that is applied to the first portion of the wavefront relative to the second portion of the wavefront.

7. The method according to claim 5, wherein determining the optical property of the point of the object from which the wavefront emanated comprises calculating an intensity of each spectral band in the wavefront that emanated from the point, by solving a set of matrices that represent the wavefront.

8. The method according to claim 5, wherein determining the optical property of the point of the object from which the wavefront emanated comprises calculating an intensity of each spectral band in the wavefront that emanated from the point, by solving a Fredholm equation that represents the wavefront.

* * * * *